Nov. 23, 1954 A. VUYK Plant Pat. 1,325
AZALEA PLANT
Filed Aug. 24, 1953
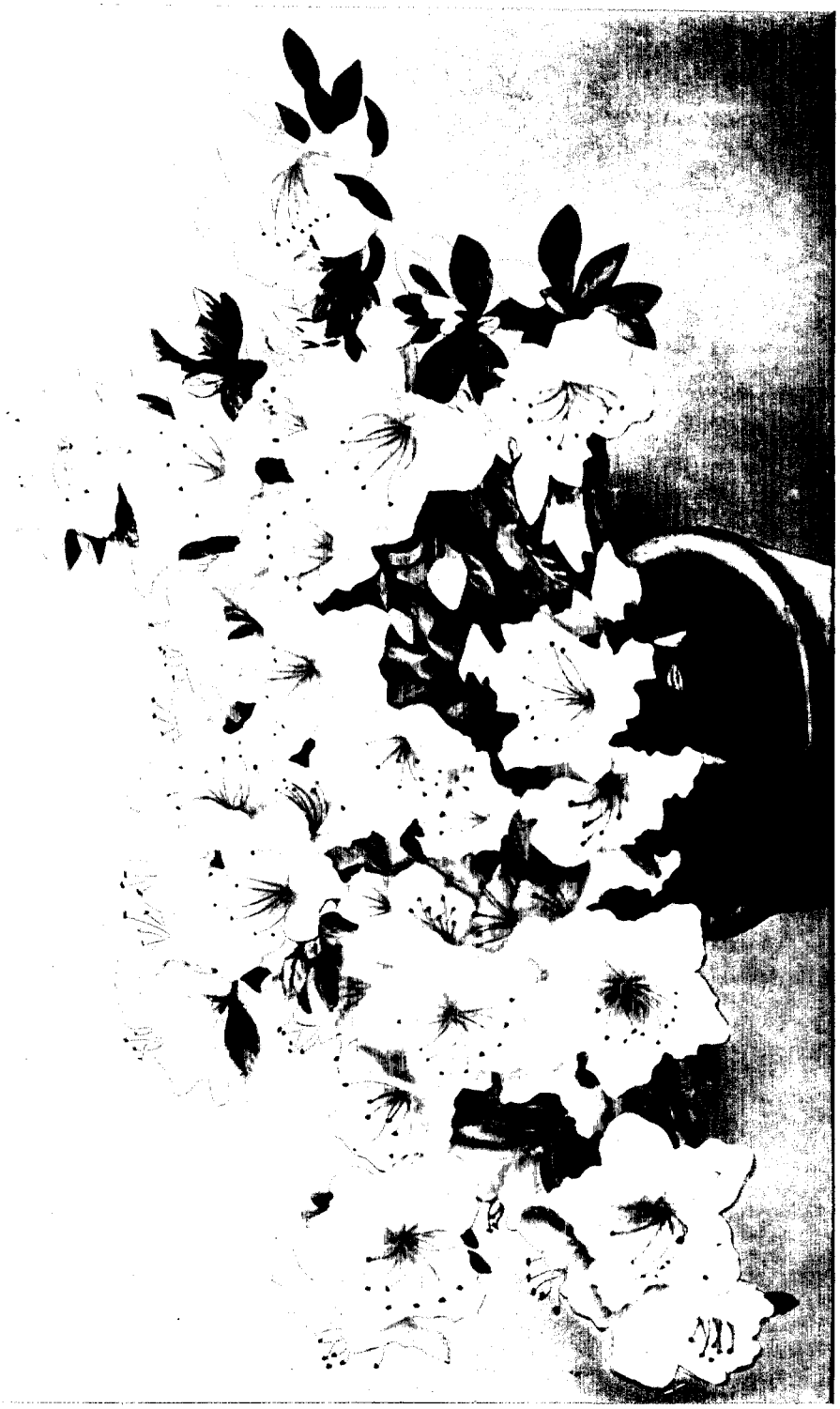
Inventor
Aart Vuyk
By: Robb & Robb
Attorneys United States Patent Office Plant Pat. 1,325

Patented Nov. 23, 1954

1,325

AZALEA PLANT

Aart Vuyk, Boskoop, Netherlands, assignor to Vuyk Van Nes, Boskoop, Netherlands, a partnership Application August 24, 1953, Serial No. 376,284

1 Claim. (Cl. 47—60)

The present invention relates to a new and distinct variety of azalea plant which was originated by me by crossing two unnamed and unpatented varieties which are identified in my breeding records by the following designations:

*Seed parent.*—VVN 128 (derived from crossing an unnamed hardy Azalea Vuykiana seedling × Azalea Macrantha Red).

*Pollen parent.*—VVN 1 (derived from crossing an unnamed hardy Azalea Vuykiana seedling × Azalea Indica Apollo).

As the result of this breeding, I have produced a new variety of azalea plant which is distinguished from its parents, as well as from all other varieties of its class of which I am aware, as evidenced by the following combination of characteristics which are outstanding in the new variety:

(1) A winter hardiness equal to the old hardy Vuykiana hybrids;

(2) The abundant production of large, glossy, heavy leaves which are deep green in summer and have a reddish green tint in the fall and winter, said leaves remaining on the plants during winter; and (3) The abundant production of flowers of brilliant rosyred general color tonality, said flowers standing erect on the flowering stems, and the flowers being notably characterized by a complete absence of fading of the color thereof.

The size and color of the flowers of my new variety most nearly resemble those of the variety of Azalea Vuykiana known as "Mrs. Vuyk Van Nes" (unpatented), but the habit and color of the leaves of my new variety are substantially identical with the leaves of the variety known as "Vuyk's Scarlet" (unpatented). The unique combination of characteristics of my new variety as noted above makes the same a valuable and desirable evergreen type of hybrid azalea of compact form for commercial use, and I have found the same to be especially suited for forcing for the Easter season.

Asexual reproduction of my new variety by cuttings at Boskoop, Holland, shows that the foregoing characteristics and distinctions come true to form and are established and transmitted through succeeding propagations.

The accompanying drawing shows a typical specimen plant of my new variety, as depicted in color, and with the flowers thereof in various stages of development, the colors being shown as nearly true as it is reasonably possible to make the same in a color illustration of this character.

The following is a detailed description of my new variety as based upon observations made in Boskoop, Holland, with color terminology in accordance with Robert F. Wilson's Horticultural Colour Chart, as issued by the British Color Council in collaboration with the Royal Horticultural Society, except where general color terms of ordinary dictionary significance are obvious:

Type: Hardy; evergreen.
Parentage: Seedling.
*Seed parent.*—An unnamed azalea designated as VVN 128.

*Pollen parent.*—An unnamed azalea designated as VVN 1.

PLANT

Form of plant: Bush; much-branched; compact.
Growth habit: Medium; branching; compact.
Rooting: Vigorous; compact.
Blooming habit: Free, resulting in profusion of blooms.
Blooming season: May; excellent for forcing, particularly for Easter season.
Foliage:
*Size.*—Medium.
*Quantity.*—Abundant.
*Color.*—New foliage: upper side—Fern Green, Plate 0862/2; under side—Pod Green, Plate 061/1. Old foliage: upper side—Parsley Green, Plate 00962/2; under side—Fern Green, Plate 0862/1.
*Shape.*—Oval pointed.
*Texture.*—Upper side—glossy. Under side—rough.
*Edge or margin.*—Smooth.
*Aspect.*—A commercially valuable and desirable evergreen hybrid azalea of compact form, with glossy leaves which are deep green color in summer and have a reddish green tint in fall and winter, and which is particularly characterized by its abundant production of brilliant rosyred flowers in spring.
*Disease resistance.*—Similar to that of hardy Vuykiana azaleas, such as "Wilhelmina Vuyk" (unpatented), "Gerardina Vuyk" (unpatented) and "Beethoven" (unpatented), as determined by comparison with these varieties growing under comparable cultural conditions at Boskoop, Holland.

FLOWER

Flowers borne: 2 to 4 to stem; in clusters; on strong, medium length stems.
Quantity of bloom: Abundant, outdoors and in greenhouse.
Continuity: One season. Permanence—3 to 4 weeks; non-fading in sun.
Petalage:
*Number of petals under normal conditions.*—4 to 6, but generally 5.
*Color of bud.*—Tyrian Rose, Plate 024.
*Color of open flower.*—Rose Madder, Plate 023/2, shading to Tyrian Rose, Plate 024/1 at center.
*Texture.*—Firm; crisp.
*Appearance.*—Inside—Rose Madder, Plate 023/2, shading to Tyrian Rose, Plate 024/1 at center. Outside—Tyrian Rose, Plate 024/1.
*Shape.*—Medium depth; slightly fringed edges; from 2½ to 3 inches in diameter.
*Arrangement.*—In clusters of generally 3 to 4 flowers which stand firmly erect.

REPRODUCTIVE ORGANS

Stamens: 7 to 10 per flower. Color—Rose Madder, Plate 023/2.
Pollen: Color—Aureolin, Plate 3/3.
Styles: 1 per flower.
Ovaries: Four.

I claim:

A new and distinct variety of azalea plant of the hardy evergreen type, substantially as herein shown and described, characterized particularly as to novelty by its winter hardiness, by its abundance of large, glossy, heavy leaves which are deep green in summer and have a reddish green tint in fall and winter and remain on the plant during winter, by its abundant production of erect flowers of brilliant rosyred general color tonality, and by the absence of fading of the flower color aforesaid.

No references cited.